United States Patent
Gross et al.

(10) Patent No.: US 8,328,879 B2
(45) Date of Patent: Dec. 11, 2012

(54) PHTHALIMIDES AS BLEACH ACTIVATORS

(75) Inventors: Wibke Gross, Hueckelhoven (DE);
Ralph Nemitz, Juechen (DE); Astrid Kroos, Monheim (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/525,477

(22) Filed: Jun. 18, 2012

(65) Prior Publication Data

US 2012/0246841 A1    Oct. 4, 2012

Related U.S. Application Data

(63) Continuation of application No. PCT/EP2010/064720, filed on Oct. 4, 2010.

(30) Foreign Application Priority Data

Dec. 18, 2009    (DE) .......................... 10 2009 054 949

(51) Int. Cl.
*D06L 3/00* (2006.01)
*C07D 209/48* (2006.01)
(52) U.S. Cl. ................. 8/101; 8/111; 548/477
(58) Field of Classification Search .............. 8/101, 111; 548/477
See application file for complete search history.

(56) References Cited

U.S. PATENT DOCUMENTS 3,969,257 A * 7/1976 Murray .................. 510/376

FOREIGN PATENT DOCUMENTS

| DE | 1091976 B | 11/1960 |
| DE | 102005003412 A1 | 8/2006 |
| EP | 0508623 A2 | 10/1992 |
| EP | 1161936 A1 | 12/2001 |
| GB | 2270690 A | 3/1994 |

OTHER PUBLICATIONS

STIC Search Report dated Aug. 7, 2012.*
English translation of the Written Opinion, dated Jun. 25, 2012, International Application PCT/EP2010/064720 All references cited in the Written Opinion are listed above.

* cited by examiner

*Primary Examiner* — Eisa Elhilo
(74) *Attorney, Agent, or Firm* — David LeCroy

(57) ABSTRACT

Agent for lightening keratin fibers, particularly human hair. The agent for lightening keratin fibers contains at least one cationic phthalimide of formula (I) in addition to an oxidant in a cosmetic carrier.

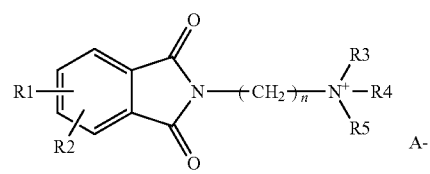

(I)

12 Claims, No Drawings

PHTHALIMIDES AS BLEACH ACTIVATORS

CROSS REFERENCE TO RELATED APPLICATIONS

The present application is a continuation of International Patent Application No. PCT/EP2010/064720 filed 4 Oct. 2010, which claims priority to German Patent Application No. 10 2009 054 949.8, filed 18 Dec. 2009, both of which are incorporated herein by reference.

BACKGROUND OF THE INVENTION

The present invention relates to agents for lightening keratinic fibers, particularly human hair, which, in addition to a chemical oxidizing agent, contain at least one specific cationic phthalimide. Use thereof on keratinic fibers significantly improves the lightening power of lightening and blonding agents. The present invention furthermore relates to a multicomponent packaging unit (kit of parts) for lightening keratinic fibers comprising, packaged separately from one another, at least one agent containing a specific cationic phthalimide, an oxidizing agent preparation and optionally a blonding powder.

Modifying the shape and color of hair is an important area of modern cosmetics and allows the appearance of the hair to be adapted both to current fashion trends and to a person's individual wishes. Permanent waves and other methods for modifying hair shape may be applied virtually irrespective of the type of hair treated. In contrast, dyeing and blonding methods are restricted to specific initial hair colors.

Lightening of the natural hair color has long been a desire of many consumers, since blonde hair color is regarded as attractive and desirable from a fashion standpoint. Various blonding agents of variable blonding power are commercially obtainable for this purpose. The oxidizing agents present in these products are capable of lightening the hair fibers by oxidative destruction of the hair's own colorant melanin. To achieve a moderate blonding effect, it is sufficient to use hydrogen peroxide, optionally together with ammonia or other alkalizing agents, as the sole oxidizing agent, while if a stronger blonding effect is desired, it is conventional to use a mixture of hydrogen peroxide and peroxodisulfate salts and/or peroxomonosulfate salts.

Unfortunately, lightening is also accompanied by hair damage as it is not only the hair's colorants which suffer oxidative damage, but also other structural components of the hair. Depending on its extent, damage can vary from rough, brittle and difficult to comb hair via reduced resistance and tensile strength of the hair to hair breakage. In general, the greater the amount of hydrogen peroxide and optional peroxodisulfates used, the more severe will be the damage caused to the keratin fibers. Hair dyes or lightening agents which exhibit good lightening power without simultaneously damaging the hair fibers are hitherto unknown.

It is accordingly an object of the present application to provide novel agents for lightening or blonding hair which are comparable or superior to the conventional agents on the market in their lightening power, while at the same time exhibiting reduced hair damage. For consumers with very dark hair, it is not possible to create light blond shades even when using elevated hydrogen peroxide concentrations in combination with persulfate salts. Repeated applications also cannot be carried out because of increasing levels of hair damage. It is therefore a further object of the present invention to provide an agent having lightening capacity which exceeds that of conventional commercial agents consisting of hydrogen peroxide and peroxodisulfate salts (sodium peroxodisulfate, ammonium peroxodisulfate and/or potassium peroxodisulfate).

EP 508623 A2 discloses specific cationic phthalimide derivatives in the form of the percarboxylic acids thereof which are used in the presence of perborates as bleaching agents in textile bleaching. Use of the corresponding phthalimides in blonding agents for lightening hair is hitherto unknown. When bleaching textiles and lightening hair, different, in some cases greatly different, application parameters are selected, such that the test results from one field of application cannot be transferred to the other. Accordingly, both the formulation and the temperatures to be selected in the two bleaching processes differ greatly. It was therefore not foreseeable from the prior art that the lightening action hair can be enhanced by using cationic phthalimides in cosmetic blonding agents.

SUMMARY OF THE INVENTION

It has now unforeseeably been found that the use of a combination of cationic phthalimide derivatives of general formula (I) and hydrogen peroxide lightens the hair much more than is possible by use of a comparable amount of hydrogen peroxide alone.

Because of the improved blonding power when the agent according to the invention is used, it is possible to reduce the amount of oxidizing agent used and thereby minimize hair damage. It is also possible to reduce exposure time while achieving a lightening effect corresponding to the prior art. These agents also have increased lightening power relative to conventional commercial lightening agents and therefore allow very dark hair to be lightened to light blond shades.

Agents according to the invention decolorize the natural colorant melanin by oxidation. Synthetic dyes previously present on or in the keratin-containing fiber may also be destroyed with the assistance of the agents according to the invention, so bleaching the fibers.

The invention therefore firstly provides an agent for lightening keratinic fibers, wherein it contains in a cosmetic carrier—
(i) at least one oxidizing agent chosen from hydrogen peroxide and/or one of the solid addition products thereof onto organic or inorganic compounds, and
(ii) at least one cationic phthalimide of the formula (I),

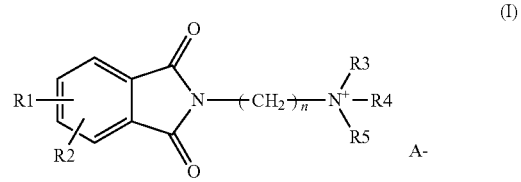

wherein
R1 and R2 in each case mutually independently are a hydrogen atom, a halogen atom, a $C_1$-$C_6$ alkyl group, a partially or completely halogenated $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group, a nitrile group, a nitroso group, a nitro group, a carboxylic acid group, a sulfonic acid group, a sulfonamido group, an amino group, a di-$C_1$-$C_6$-alkylamino group, a mono-$C_1$-$C_6$-alkylamino group, a $C_1$-$C_6$ alkoxycarbonyl group, an optionally substituted aryl group, or an optionally substituted heteroaryl group, or R1 and R2 form, together with the adjacent benzene ring, a further phthalimide unit of the formula (Ia),

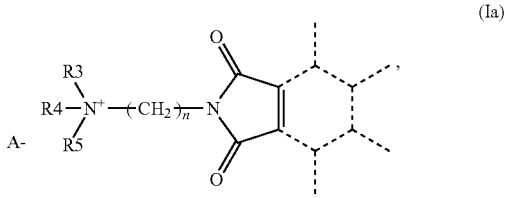

(Ia)

R3, R4, R5 in each case mutually independently are a $C_1$-$C_6$ alkyl group, a partially or completely halogenated $C_1$-$C_6$ alkyl group, a $C_2$-$C_6$ alkenyl group, a $C_2$-$C_6$ hydroxyalkyl group, a $C_2$-$C_6$ polyhydroxyalkyl group, a $C_1$-$C_6$-alkoxy-$C_2$-$C_6$-alkyl group, a cyano-$C_1$-$C_6$-alkyl group, an aryl-$C_1$-$C_6$-alkyl group, a carboxy-$C_1$-$C_6$-alkyl group or a sulfonyl-$C_1$-$C_6$-alkyl group or two of the substituents R3, R4 and R5 form, together with the attached nitrogen, a 5-, 6- or 7-membered, saturated or unsaturated ring which optionally contains further heteroatoms, n is an integer from 1 to 6 and $A^-$ is a physiologically acceptable anion.

DETAILED DESCRIPTION OF THE INVENTION

Keratinic fibers refer to furs, wool, feathers and particularly human hair. Although agents according to the invention are primarily suitable for lightening keratin fibers, there is no reason in principle why they should not also be used in other fields.

Agents according to the invention contain the active ingredients in a cosmetic carrier. This cosmetic carrier is preferably aqueous, alcoholic or aqueous-alcoholic. Carriers suitable for the purpose of hair bleaching include creams, emulsions, gels or surfactant-containing foaming solutions such as shampoos, foam aerosols or other preparations suitable for use on the hair. It is also possible to provide a formulation in pulverulent or tablet form, which is preferred for lightening agents. The formulation is then mixed prior to use in an aqueous solvent or with organic solvents or with mixtures of water and organic solvents to obtain the application mixture. An aqueous carrier according to the invention contains at least 40 wt. %, particularly at least 50 wt. %, water. For the purposes of the present invention, aqueous-alcoholic solutions are aqueous solutions containing 3 to 70 wt. % of a $C_1$-$C_4$ alcohol, particularly ethanol or isopropanol. Agents according to the invention may additionally contain further organic solvents such as 4-methoxybutanol, diethylene glycol monoethyl ether, 1,2-propylene glycol, n-propanol, n-butanol, n-butylene glycol, glycerol, diethylene glycol monoethyl ether, and diethylene glycol mono-n-butyl ether. All water-soluble organic solvents are preferred. Preferred agents according to the invention additionally contain a nonaqueous solvent, wherein particularly preferred agents according to the invention contain the solvent in a concentration of 0.1-30 wt. %, preferably in a concentration of 1-20 wt. %, more preferably in a concentration of 2-10 wt. %, relative to the agent.

As a first ingredient, the agent according to the invention contains hydrogen peroxide and/or one of the solid addition products thereof onto organic or inorganic compounds. In a preferred embodiment, hydrogen peroxide itself is used as an aqueous solution. Hydrogen peroxide may, however, also be used in the form of a solid addition compound of hydrogen peroxide on inorganic or organic compounds such as sodium perborate, sodium percarbonate, magnesium percarbonate, sodium percarbamide, polyvinylpyrrolidinone n $H_2O_2$ (n is a positive integer greater than 0), urea peroxide and melamine peroxide. In the latter-stated case, the addition compounds liberate hydrogen peroxide in the application mixture according to the invention (i.e., in addition to the addition compound, these agents contain free hydrogen peroxide in the cosmetic carrier).

According to the invention, hydrogen peroxide is preferably added to the agent as aqueous hydrogen peroxide solution. In one embodiment of the first subject matter of the invention, the agent contains an aqueous solution of hydrogen peroxide as the oxidizing agent.

The concentration of a hydrogen peroxide solution is determined by statutory requirements and by the desired effect. 6 to 12 wt. % solutions in water are preferably used. Preferred agents contain, relative to the total weight thereof, 0.01 to 12 wt. %, preferably 0.1 to 10 wt. %, more preferably 1 to 6 wt. % of hydrogen peroxide (calculated as 100% $H_2O_2$).

As a further ingredient to the invention, the agents contain at least one cationic phthalimide of formula (I). Examples of residues stated as substituents for the compounds of formula (I) are listed hereafter:

Examples of halogen atoms are fluorine, chlorine, bromine and iodine;

Examples of $C_1$-$C_6$ alkyl residues are the groups —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)$ $CH_2CH_3$, —$C(CH_3)_3$, preferably methyl and ethyl;

Examples of partially or completely halogenated $C_1$-$C_6$ alkyl residues are —$CH_2F$, —$CH_2Cl$, —$CF_3$, —$CH_2CF_3$, —$CF_2CF_3$ or —$CH(CF_3)_2$, particularly —$CF_3$;

Examples of a $C_2$-$C_6$ alkenyl group are prop-2-enyl (allyl), 2-methylprop-2-enyl, but-3-enyl, but-2-enyl, penta-4-enyl or penta-3-enyl, preferably prop-2-enyl;

Examples of a $C_2$-$C_6$ hydroxyalkyl group are —$CH_2CH_2OH$, —$CH_2CH_2CH_2OH$, —$CH_2CH(OH)$ $CH_3$, —$CH_2CH_2CH_2CH_2OH$, in particular —$CH_2CH_2OH$;

Examples of suitable $C_2$-$C_6$ polyhydroxyalkyl groups are —$CH(OH)CH_2OH$, —$CH_2CH(OH)CH_2OH$, —$CH(OH)CH(OH)CH_3$, —$CH_2CH_2CH(OH)CH_2OH$, preferably —$CH_2CH(OH)CH_2OH$;

Examples of $C_1$-$C_6$ alkoxy groups are —$OCH_3$, —$OCH_2CH_3$, —$OCH(CH_3)_2$, —$OC(CH_3)_3$, preferably —$OCH_3$;

Examples of $C_1$-$C_6$-alkoxy-$C_2$-$C_6$-alkyl groups are —$CH_2CH_2OCH_3$, —$CH_2CH_2CH_2OCH_3$, —$CH_2CH_2OCH_2CH_3$, —$CH_2CH_2CH_2OCH_2CH_3$, —$CH_2CH_2OCH(CH_3)_2$, —$CH_2CH_2CH_2OCH(CH_3)_2$;

Examples of a di-$C_1$-$C_6$-alkylamino group are —$N(CH_3)_2$, —$N(CH_2CH_3)_2$, —$N(CH_2CH_2CH_3)_2$, —$N(CH_2CH_3)$ $CH_3$, —$N(CH_3)[CH(CH_3)_2]$;

Examples of a mono-$C_1$-$C_6$-alkylamino group are —$NH(CH_3)$, —$NH(CH_2CH_3)$, —$NH(CH_2CH_2CH_3)$, —$NH\{C(CH_3)\}_3$, —$NH\{CH(CH_3)_2\}$;

Examples of a $C_1$-$C_6$ alkoxycarbonyl group are —$CO_2CH_3$, —$CO_2CH_2CH_3$, —$CO_2CH(CH_3)_2$, —$CO_2C(CH_3)_3$;

Examples of a cyano-$C_1$-$C_6$-alkyl group are —$CH_2CN$, —$CH_2CH_2CN$, —$CH_2CH_2CH_2CN$;

Examples of a carboxy-$C_1$-$C_6$-alkyl group are —$CH_2CO_2H$, —$CH_2CH_2CO_2H$, —$CH_2CH_2CH_2CO_2H$;

Examples of a sulfonyl-$C_1$-$C_6$-alkyl group are —$CH_2SO_3H$, —$CH_2CH_2SO_3H$, —$CH_2CH_2CH_2SO_3H$;

Examples of aryl-$C_1$-$C_6$-alkyl groups are benzyl and 2-phenylethyl;

Examples of an aryl group are phenyl, 1-naphthyl or 2-naphthyl;

Examples of a heteroaryl group are pyridin-2-yl, pyridin-3-yl, pyridin-4-yl, pyrimidin-2-yl, pyrrol-1-yl, pyrrol-2-yl, pyrrol-3-yl, pyrazol-1-yl, pyrazol-3-yl or pyrazol-4-yl.

In one embodiment the agent contains as the phthalimide according to formula (I) at least one compound wherein R1 and R2 in each case mutually independently are a hydrogen atom, a halogen atom, a hydroxyl group, a $C_1$-$C_6$ alkoxy group, particularly a hydrogen atom, or R1 and R2 form, together with the adjacent benzene ring, a further phthalimide unit of formula (Ia).

In a further embodiment of the present invention the agent contains as the phthalimide according to formula (I) at least one compound wherein R3, R4 and R5 in each case mutually independently are a $C_1$-$C_6$ alkyl group, a $C_2$-$C_6$ alkenyl group or a $C_2$-$C_6$ hydroxyalkyl group.

Preferred compounds of formula (I) are chosen from compounds 1 to 28 (Table 1)—

| | |
|---|---|
| 1 | 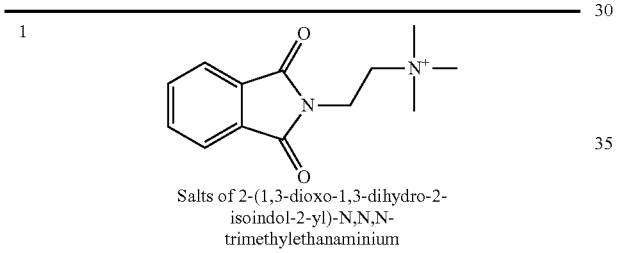<br>Salts of 2-(1,3-dioxo-1,3-dihydro-2-isoindol-2-yl)-N,N,N-trimethylethanaminium |
| 2 | 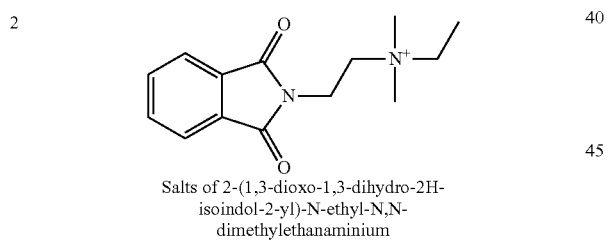<br>Salts of 2-(1,3-dioxo-1,3-dihydro-2H-isoindol-2-yl)-N-ethyl-N,N-dimethylethanaminium |
| 3 | 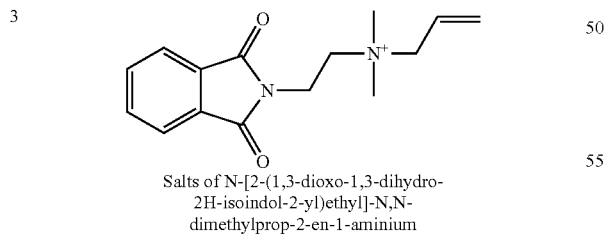<br>Salts of N-[2-(1,3-dioxo-1,3-dihydro-2H-isoindol-2-yl)ethyl]-N,N-dimethylprop-2-en-1-aminium |
| 4 | 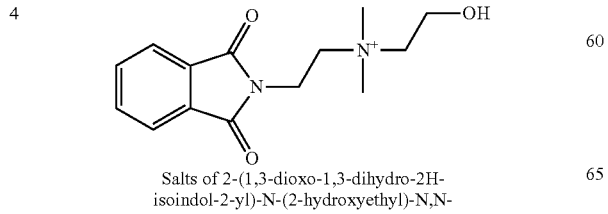<br>Salts of 2-(1,3-dioxo-1,3-dihydro-2H-isoindol-2-yl)-N-(2-hydroxyethyl)-N,N-dimethylethanaminium |
| 5 | 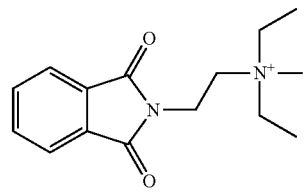<br>Salts of 2-(1,3-dioxo-1,3-dihydro-2-isoindol-2-yl)-N,N-diethyl-N-methylethanaminium |
| 6 | 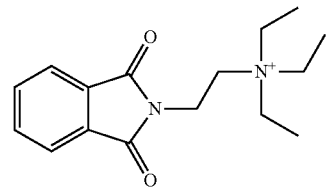<br>Salts of 2-(1,3-dioxo-1,3-dihydro-2H-isoindol-2-yl)-N,N,N-triethylethanaminium |
| 7 | 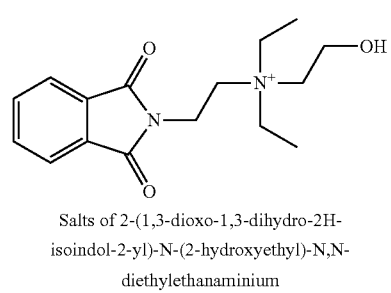<br>Salts of N-[2-(1,3-dioxo-1,3-dihydro-2H-isoindol-2-yl)ethyl]-N,N-diethylprop-2-en-1-aminium |
| 8 | 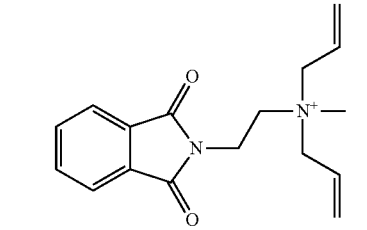<br>Salts of 2-(1,3-dioxo-1,3-dihydro-2H-isoindol-2-yl)-N-(2-hydroxyethyl)-N,N-diethylethanaminium |
| 9 | 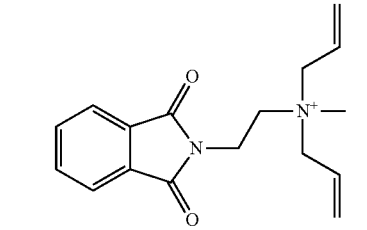<br>Salts of N-allyl-N-[2-(1,3-dioxo-1,3-dihydro-2H-isoindol-2-yl)ethyl]-N-methylprop-2-en-1-aminium |

10
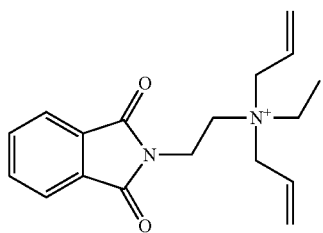
Salts of N-allyl-N-[2-(1,3-dioxo-1,3-dihydro-2H-isoindol-2-yl)ethyl]-N-ethylprop-2-en-1-aminium 11
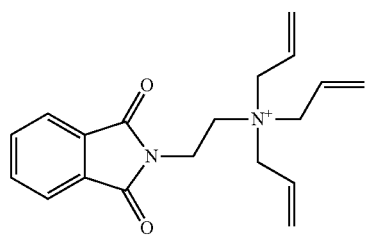
Salts of N,N-diallyl-N-[2-(1,3-dioxo-1,3-dihydro-2H-isoindol-2-yl)ethyl]prop-2-en-1-aminium 12
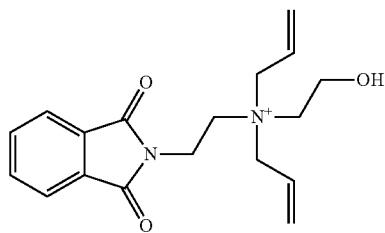
Salts of N-allyl-N-[2-(1,3-dioxo-1,3-dihydro-2H-isoindol-2-yl)ethyl]-N-(2-hydroxyethyl)-prop-2-en-1-aminium 13
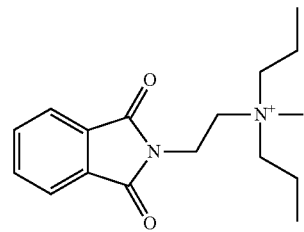
Salts of N-[2-(1,3-dioxo-1,3-dihydro-2H-isoindol-2-yl)ethyl]-N-methyl-N-propylpropan-1-aminium 14
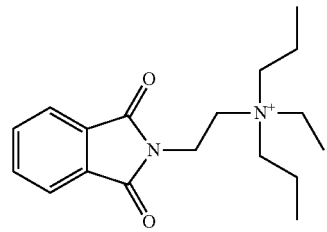
Salts of N-[2-(1,3-dioxo-1,3-dihydro-2H-isoindol-2-yl)ethyl]-N-ethyl-N-propylpropan-1-aminium 15
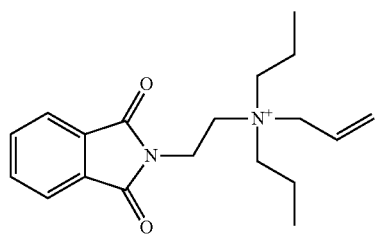
Salts of N-[2-(1,3-dioxo-1,3-dihydro-2H-isoindol-2-yl)ethyl]-N,N-dipropylprop-2-en-1-aminium 16
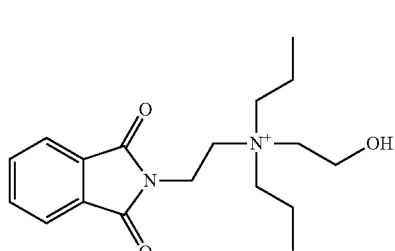
Salts of N-[2-(1,3-dioxo-1,3-dihydro-2H-isoindol-2-yl)ethyl]-N-(2-hydroxyethyl)-N-propylpropan-1-aminium 17
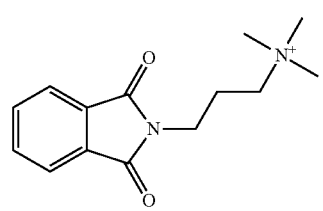
Salts of 3-(1,3-dioxo-1,3-dihydro-2H-isoindol-2-yl)-N,N,N-trimethylpropan-1-aminium 18
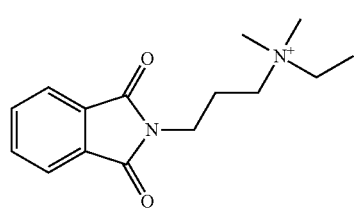
Salts of 3-(1,3-dioxo-1,3-dihydro-2H-isoindol-2-yl)-N-ethyl-N,N-dimethylpropan-1-aminium 19
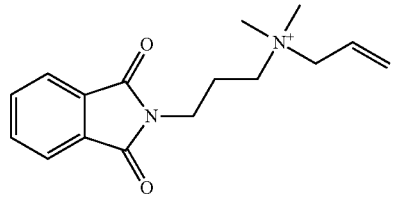
Salts of N-[3-(1,3-dioxo-1,3-dihydro-2H-isoindol-2-yl)propyl]-N,N-dimethylprop-2-en-1-aminium

20

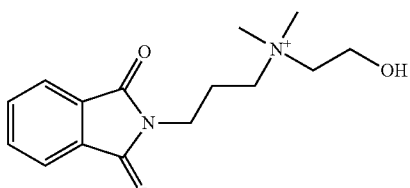

Salts of 3-(1,3-dioxo-1,3-dihydro-2H-
isoindol-2-yl)-N-(2-hydroxyethyl)-N,N-
dimethylpropan-1-aminium

21

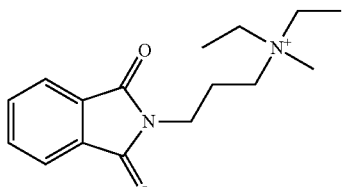

Salts of 3-(1,3-dioxo-1,3-dihydro-2H-
isoindol-2-yl)-N,N-diethyl-N-
methylpropan-1-aminium

22

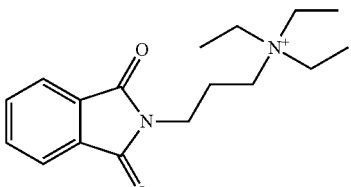

Salts of 3-(1,3-dioxo-1,3-dihydro-2H-
isoindol-2-yl)-N,N,N-triethylpropan-1-
aminium

23

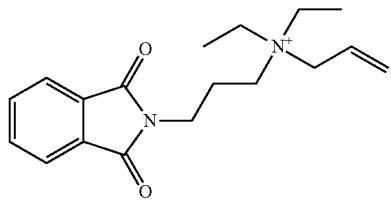

Salts of N-[3-(1,3-dioxo-1,3-dihydro-
2H-isoindol-2-yl)propyl]-N,N-
diethylprop-2-en-1-aminium

24

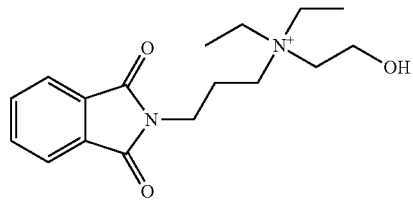

Salts of 3-(1,3-dioxo-1,3-dihydro-2H-
isoindol-2-yl)-N,N-diethyl-N-(2-
hydroxyethyl)-propan-1-aminium

25

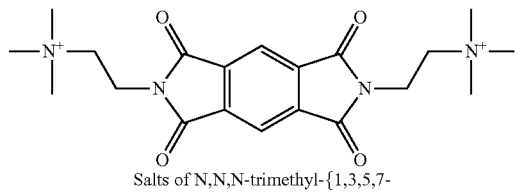

Salts of N,N,N-trimethyl-{1,3,5,7-
tetraoxo-6-[2-
(trimethylammonio)ethyl]-3,5,6,7-
tetrahydropyrrolo[3,4-f]isoindol-
2(1H)-yl}ethan-2-aminium

26

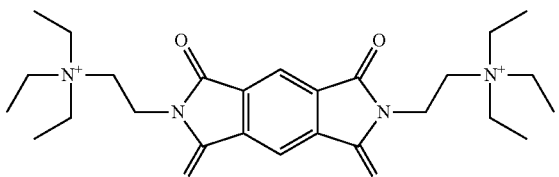

Salts of N,N,N-triethyl-{1,3,5,7-
tetraoxo-6-[2-(triethylammonio)ethyl]-
3,5,6,7-tetrahydropyrrolo[3,4-f]isoindol-
2(1H)-yl}ethan-2-aminium

27

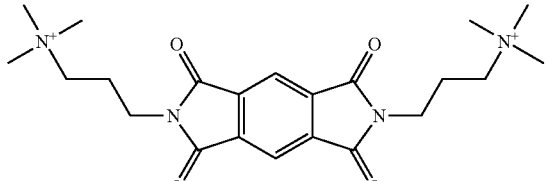

Salts of N,N,N-trimethyl-{1,3,5,7-
tetraoxo-6-[3-(trimethylammonio)-
propyl]-3,5,6,7-tetrahydropyrrolo-
[3,4-f]isoindol-2(1H)-yl}propan-2-
aminium

28

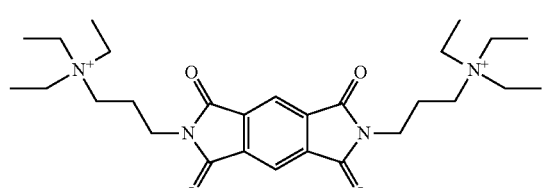

Salts of N,N,N-triethyl-{1,3,5,7-
tetraoxo-6[3-(triethylammonio)-propyl]-
3,5,6,7-tetrahydropyrrolo-[3,4-f]isoindol-
2(1H)-yl}propan-2-aminium Preferred agents are those which, in addition to at least one oxidizing agent chosen from hydrogen peroxide and/or one of the solid addition products thereof onto organic or inorganic compounds, contain in a cosmetic carrier at least one of the compounds chosen from the group of physiologically acceptable salts, the cationic moieties of which are formed of salts of 2-(1,3-dioxo-1,3-dihydro-2-isoindol-2-yl)-N,N,N-trimethylethanaminium, salts of 2-(1,3-dioxo-1,3-dihydro-2H-isoindol-2-yl)-N,N-diethyl-N-methylethanaminium, salts of N-[2-(1,3-dioxo-1,3-dihydro-2H-isoindol-2-yl)ethyl]-N,N-diethylprop-2-en-1-aminium, salts of N-allyl-N-[2-(1,3-dioxo-1,3-dihydro-2H-isoindol-2-yl)ethyl]-N-methylprop-2-en-1-aminium, salts of N-[2-(1,3-dioxo-1,3-dihydro-2H-isoindol-2-yl)ethyl]-N-methyl-N-propylpropan-1-aminium, salts of N-[2-(1,3-dioxo-1,3-dihydro-2H-isoindol-2-yl)ethyl]-N,N-dipropylprop-2-en-1-aminium, salts of 3-(1,3-dioxo-1,3-dihydro-2H-isoindol-2-yl)-N,N,N-trimethylpropan-1-aminium, salts of N-[3-(1,3-dioxo-1,3-dihydro-2H-isoindol-2-yl)propyl]-N,N-dimethylprop-2-en-1-aminium, salts of 3-(1,3-dioxo-1,3-dihydro-2H-isoindol-2-yl)-N,N-diethyl-N-methylpropan-1-aminium and salts of N-[3-(1,3-dioxo-1,3-dihydro-2H-isoindol-2-yl)propyl]-N,N-diethyl-prop-2-en-1-aminium.

In a preferred embodiment of the first subject matter of the invention the agent contains as the phthalimide according to formula (I) at least 2-(1,3-dioxo-1,3-dihydro-2H-isoindol-2-yl)-N,N-diethyl-N-methylethanaminium p-toluenesulfonate, N-allyl-N-[2-(1,3-dioxo-1,3-dihydro-2H-isoindol-2-yl)ethyl]-N-methylprop-2-en-1-aminium p-toluenesulfonate and N-[2-(1,3-dioxo-1,3-dihydro-2H-isoindol-2-yl)ethyl]-N-methyl-N-propylpropan-1-aminium p-toluenesulfonate.

Preferably, agents according to the invention contain the phthalimide(s) of formula (I) in an amount of 0.01 to 25 wt. %, particularly 0.1 to 10 wt. % and more particularly 0.5 to 5.0 wt. %, relative to total weight of the ready-to-use agent.

Agents according to the invention may also be produced from two or more separately packaged preparations directly before application. This is particularly appropriate for separating incompatible ingredients, thereby avoiding a premature reaction. One conventional way therefore involves mixing a first agent containing at least one phthalimide of general formula (I) directly before application with a second agent containing oxidizing agent(s) according to the invention.

The present invention accordingly also provides an agent for lightening keratinic fibers, particularly human hair, which is obtained immediately before application onto the hair from a flowable preparation (A) containing a cationic phthalimide of general formula (I) and an oxidizing agent preparation (B) containing at least one oxidizing agent chosen from hydrogen peroxide and/or the addition compounds thereof onto organic or inorganic compounds.

Oxidizing agent preparation (B) is preferably an aqueous, flowable oxidizing agent preparation. In preferred agents according to the invention for lightening keratinic fibers, the flowable oxidizing agent preparation B contains, relative to its weight, 40 to 90 wt. %, preferably 50 to 85 wt. %, particularly preferably 55 to 80 wt. %, more preferably 60 to 77.5 wt. % and particularly 65 to 75 wt. % water.

The lightening power of agents according to the invention is distinctly increased by use of cationic phthalimides according to formula (I), so that under certain circumstances it is possible to dispense with the addition of further bleach boosters, thereby resulting in reduced hair damage.

When particularly strong lightening is required, particularly for very dark, strongly pigmented initial hair colors, it may, however, be necessary to incorporate additional bleach boosters into the agent. If such strong lightening is desired, it is preferred to additionally add a blonding preparation (C) containing at least one bleach booster to the mixture of oxidizing agent preparation (B) and preparation (A). It may be immaterial whether a mixture of (A) and (B) is firstly produced and then the blonding preparation (C) is mixed in, or whether the individual components are mixed in a different sequence. It is preferred to mix the individual preparations in as rapid a succession as possible, and to apply the ready-to-use agent promptly onto the keratinic fibers.

A further embodiment of the present application is therefore an agent for bleaching keratinic fibers produced by mixing at least one oxidizing agent preparation (B), containing at least one oxidizing agent chosen from hydrogen peroxide and the addition compounds thereof onto solid carriers, at least one blonding preparation (C), containing at least one bleach booster, and at least one preparation (A), wherein preparation (A) contains in a cosmetic carrier at least one cationic phthalimide according to formula (I).

For the purposes of the present invention, additional bleach boosters of blonding preparation (C) which may be used are peroxo compounds, as well as compounds which, under perhydrolysis conditions, yield aliphatic peroxycarboxylic acids and/or substituted perbenzoic acid, carbonic acid derivatives, alkyl carbonates/carbamates, silyl carbonates and carbamates.

The bleach booster is preferably chosen from ammonium peroxodisulfate, alkali metal peroxodisulfates, ammonium peroxomonosulfate, alkali metal hydrogenperoxomonosulfates, alkali metal peroxodiphosphates and alkaline earth metal peroxides. Particularly preferred bleach boosters are ammonium peroxodisulfate, potassium peroxodisulfate, sodium peroxodisulfate, potassium hydrogenperoxomonosulfate, potassium peroxodiphosphate, magnesium peroxide and barium peroxide.

Particularly preferred agents according to the invention are those containing at least one inorganic salt chosen from peroxomonosulfates and/or peroxydisulfates as bleach booster in the blonding preparation (C). It is furthermore particularly preferable for agents according to the invention to contain at least two different peroxydisulfates. Preferred peroxodisulfate salts are here combinations of ammonium peroxodisulfate and potassium peroxodisulfate and/or sodium peroxodisulfate. Accordingly, in a further embodiment of this subject matter of the invention the lightening agent additionally contains at least one inorganic persulfate or peroxydisulfate salt, particularly ammonium peroxodisulfate, potassium peroxodisulfate and/or sodium peroxodisulfate. The peroxo compounds are present in an amount of 0.1 to 25 wt. %, particularly 0.5 to 15 wt. %, based on total weight of the ready-to-use agent. The persulfate salts or peroxodisulfate salts are generally used in the form of an optionally dedusted powder, a paste or in the form of a pressed molding.

Anhydrous compositions according to the invention may also contain a bleach booster instead of and/or in addition to the solid peroxo compounds.

Bleach boosters which may be used are compounds which, under perhydrolysis conditions, yield aliphatic peroxycarboxylic acids with preferably 1 to 10 C atoms, particularly 2 to 4 C atoms, and/or optionally substituted perbenzoic acid. Suitable substances are those bearing O- and/or N-acyl groups having the stated number of C atoms and/or optionally substituted benzoyl groups. Preferred compounds are repeatedly acylated alkylenediamines, particularly tetraacetylethylenediamine (TAED), acylated triazine derivatives, particularly 1,5-diacetyl-2,4-dioxohexahydro-1,3,5-triazine (DADHT), acylated glycolurils, particularly tetraacetylglycoluril (TAGU), N-acylimides, particularly N-nonanoylsuccinimide (NOSI), acylated phenolsulfonates, particularly n-nonanoyl- or isononanoyloxybenzenesulfonate (n- or i-NOBS), carboxylic anhydrides, particularly phthalic anhydride, acylated polyhydric alcohols, particularly triacetin, ethylene glycol diacetate and 2,5-diacetoxy-2,5-dihydrofuran.

Carbonate salts or hydrogencarbonates may preferably be used according to the invention as bleach boosters of the carbonic acid derivative type. These are preferably chosen from ammonium, alkali metal (particularly sodium and potassium) and alkaline earth metal (particularly calcium) carbonate salts or hydrogencarbonate salts. Particularly preferred carbonate or hydrogencarbonate salts are ammonium hydrogencarbonate, ammonium carbonate, sodium hydrogencarbonate, sodium carbonate, potassium hydrogencarbonate, potassium carbonate, magnesium carbonate and calcium carbonate. These preferred salts can be used alone or in mixtures of at least two representatives thereof as bleach boosters.

At least one compound chosen from acetic acid, lactic acid, tartaric acid, citric acid, salicylic acid and ortho-phthalic acid can be present in compositions according to the invention as further additional bleach boosters.

The bleach boosters used in addition to or instead of peroxo compounds are preferably present in the cosmetic agents in amounts of 0.05 to 10 wt. %, particularly 0.2 to 5 wt. %, based on total weight of the ready-to-use agent.

Although no restrictions apply in principle regarding the formulation of the blonding preparation (C), it is preferred according to the invention for preparation (C) to be of anhydrous formulation.

For the purposes of the present invention, anhydrous means a water content relative to preparation (C) of 5 wt. % or less, particularly 2 wt. % or less. Blonding preparations which contain 0.1 wt. % or less of water may be very particularly preferred according to the invention. Preparation (C) is preferably formulated in anhydrous form as a powder or as a paste.

In an anhydrous formulation, it has proved particularly preferable for preparation (C) to contain at least one non-hydroxylated fatty acid ester with a melting point of at most 50° C., particularly at most 30° C., and/or at least one $C_{10}$-$C_{30}$ fatty acid with at least one additional hydroxyl group and/or a derivative thereof. According to the invention, esters of non-hydroxylated $C_6$-$C_{30}$ alkyl monocarboxylic acids with $C_2$-$C_{30}$ monoalcohols are preferably suitable as fatty acid esters. Particular preference is given to isopropyl myristate, cetearyl isononanoate, 2-ethylhexyl palmitate, stearic acid 2-ethylhexyl ester, cetyl oleate, coconut fatty alcohol caprinate/caprylate, n-butyl stearate, oleyl erucate, isopropyl palmitate, oleyl oleate, lauric acid hexyl ester, myristyl myristate, cetearyl isononanoate, oleic acid decyl ester.

Blonding processes on keratin fibers conventionally proceed in an alkaline environment. However, establishing an excessively high pH value is not desirable if the keratin fibers and the skin are to be treated as gently as possible. It is therefore preferred for the pH value of the ready-to-use agent to be from 7 to 11, particularly from 8 to 10.5. The pH values for the purposes of the present invention are pH values measured at a temperature of 22° C.

Alkalizing agents usable according to the invention for establishing the preferred pH value can be chosen from ammonia, alkanolamines, basic amino acids, together with inorganic alkalizing agents such as alkali(ne earth) metal hydroxides, alkali(ne earth) metal metasilicates, alkali(ne earth) metal phosphates and alkali(ne earth) metal hydrogenphosphates. Preferably used metal ions are lithium, sodium and/or potassium. Organic alkalizing agents which can be used according to the invention are preferably chosen from alkanolamines prepared from primary, secondary or tertiary amines with a $C_2$-$C_6$ alkyl parent substance having at least one hydroxyl group. Preferred alkanolamines are monoethanolamine, 2-amino-2-methylpropanol and triethanolamine. The basic amino acids usable as alkalizing agents according to the invention are preferably chosen from arginine, lysine, ornithine and histidine, particularly preferably arginine. It has, however, proved that preferred agents according to the invention additionally contain an organic alkalizing agent. In one embodiment of the first subject matter of the invention the agent additionally contains at least one alkalizing agent chosen from ammonia, alkanolamines and basic amino acids, particularly from ammonia, monoethanolamine and arginine or the compatible salts thereof.

It has been found that the blonding power of the agents can be further increased if the lightening agent contains at least one aromatic, organic solvent. Aromatic solvents for the purposes of the invention are those compounds having an aromatic structural unit, such as a phenyl group, in their structural formula and are furthermore liquid under standard conditions, namely room temperature and standard pressure. These preferably comprise carbocyclic solvents which preferably additionally bear a hydroxyl group. Preferred examples of such aromatic solvents are alcohols such as benzyl alcohol, 2-phenylethyl alcohol, 1-phenylethyl alcohol, 2-phenoxyethanol, 3-methylbenzyl alcohol, 2-methoxybenzyl alcohol and 3-methoxybenzyl alcohol.

One particularly preferred aromatic solvent according to the invention is benzyl alcohol. Preferred agents according to the invention are those which contain 0.01 to 15 wt. %, particularly 0.1 to 10 wt. % and more particularly 0.5 to 5.0 wt. %, based on total weight of the ready-to-use agent, of at least one aromatic, organic solvent.

According to the invention, the lightening agent can be applied onto the hair together with a catalyst. Such catalysts include specific enzymes, particularly peroxidases, iodides, quinones or metal ions such as $Zn^{2+}$, $Cu^{2+}$, $Fe^{2+}$, $Fe^{3+}$, $Mn^{2+}$, $Mn^{4+}$, $Li+$, $Mg^{2+}$, $Ca^{2+}$, $Ce^{4+}$, $V^{3+}$, $Co^{2+}$, $Ru^{3+}$ and $Al^{3+}$, particularly $Zn^{2+}$, $Cu^{2+}$ and $Mn^{2+}$.

It is also advantageous for the lightening agent to contain at least one stabilizer or complexing agent. Particularly preferred stabilizers are phenacetin, alkali metal benzoates (sodium benzoate) and salicylic acid. Any prior art complexing agents can also be used. These can belong to different chemical groups. They are preferably used individually or in combination with one another. Preferred complexing agents are polycarboxylic acids, particularly EDTA, and phosphonates, preferably hydroxyalkane- or aminoalkanephosphonates and particularly 1-hydroxyethane-1,1-diphosphonate (HEDP) or the di- or tetrasodium salt thereof and/or ethylenediaminetetramethylenephosphonate (EDTMP) or the hexasodium salt thereof and/or diethylenetriaminepentamethylenephosphonate (DTPMP) or the hepta- or octasodium salt thereof.

The ready-to-use lightening agents can also contain additional active ingredients, auxiliary substances and additives.

The ready-to-use lightening agents are preferably prepared as a flowable preparation with an emulsifier or a surfactant preferably added thereto; the surface-active substances being designated as, depending area of application, surfactants or emulsifiers and being chosen from anionic, cationic, zwitterionic, amphoteric and nonionic surfactants and emulsifiers.

Preferred agents according to the invention additionally contain at least one anionic surfactant. Preferred anionic surfactants are fatty acids, alkyl sulfates, alkyl ether sulfates and ether carboxylic acids with 10 to 20 C atoms in the alkyl group and up to 16 glycol ether groups per molecule. The anionic, nonionic, zwitterionic or amphoteric surfactants are used in amounts of 0.1 to 45 wt. %, preferably 1 to 30 wt. %, and very particularly preferably 1 to 15 wt. %, based on total quantity of the ready-to-use agent.

Preferred agents according to the invention additionally contain at least one zwitterionic surfactant. Particularly suitable zwitterionic surfactants are "betaines" and N-alkyl-N,N-dimethylammonium glycinates, N-acylaminopropyl-N,N-dimethylammonium glycinates, and 2-alkyl-3-carboxymethyl-3-hydroxyethylimidazolines. One preferred zwitterionic surfactant is the fatty acid amide derivative known by the INCI name Cocamidopropyl Betaine.

Preferred agents according to the invention additionally contain at least one amphoteric surfactant. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids. Particularly preferred amphoteric surfactants are N-cocoalkyl aminopropionate, cocoacylaminoethyl aminopropionate and $C_{12}$-$C_{18}$ acyl sarcosine.

It is also advantageous for the agents to contain further non-ionogenic interfacially active substances. Preferred nonionic surfactants are alkyl polyglycosides together with alkylene oxide addition products onto saturated linear fatty alcohols and fatty acids with, in each case, 2 to 30 mol of ethylene oxide per mol of fatty alcohol or fatty acid, respectively. Preparations having excellent properties are likewise obtained if they contain fatty acid esters of ethoxylated glycerol as the nonionic surfactants.

Nonionic, zwitterionic or amphoteric surfactants are used in amounts of 0.1 to 45 wt. %, preferably 1 to 30 wt. %, and very particularly preferably 1 to 15 wt. %, based on total amount of the ready-to-use agents.

Suitable agents can also contain cationic surfactants of the quaternary ammonium compound, ester quat and amidoamine type. Preferred quaternary ammonium compounds are ammonium halides, and the imidazolinium compounds known under the INCI names Quaternium-27 and Quaternium-83. Quaternized protein hydrolysates are further cationic surfactants which are usable according to the invention. One amidoamine compound which is particularly suitable according to the invention is stearamidopropyldimethylamine, commercially available under the name Tegoamid® S 18. Preferred ester quats are quaternized ester salts of fatty acids with triethanolamine, quaternized ester salts of fatty acids with diethanolalkylamines and quaternized ester salts of fatty acids with 1,2-dihydroxypropyldialkylamines. Such products are distributed, for example, under the trademarks Stepantex®, Dehyquart® and Armocare®. Agents according to the invention preferably contain cationic surfactants in amounts of 0.05 to 10 wt. %, based on total agent. Quantities of 0.1 to 5 wt. % are particularly preferred.

The ready-to-use lightening agents can contain further auxiliary substances and additives. It is advantageous for the agent to contain at least one thickener. No restrictions apply in principle with regard to these thickeners. Both organic and purely inorganic thickeners can be used.

Suitable thickeners are—
anionic, synthetic polymers;
cationic, synthetic polymers;
naturally occurring thickeners, such as nonionic guar gums, scleroglucan gums or xanthan gums, gum arabic, gum ghatti, karaya gum, tragacanth gum, carrageenan gum, agar-agar, locust bean flour, pectins, alginates, starch fractions and derivatives such as amylose, amylopectin and dextrins, together with cellulose derivatives, such as methylcellulose, carboxyalkylcelluloses and hydroxyalkylcelluloses;
nonionic, fully synthetic polymers such polyvinyl alcohol or polyvinylpyrrolidinone; and
inorganic thickeners, particularly phyllosilicates such as bentonite, particularly smectites, such as montmorillonite or hectorite.

Lightening can be further increased by additionally adding at least one $SiO_2$ compound, such as silica or silicates, particularly water glasses, to the composition according to the invention. It can be preferred to use the $SiO_2$ compounds in amounts of 0.05 wt. % to 15 wt. %, more preferably 0.15 wt. % to 10 wt. %, and very preferably 0.2 wt. % to 5 wt. %, relative to the anhydrous composition, according to the invention. The stated quantities here indicate the content of $SiO_2$ compounds (excluding their water content) in the agents.

Furthermore, in order to dull unwanted residual color impressions, particularly in the reddish or bluish range, the lightening agents can contain specific, direct dyes of the complementary colors. These are dyes which key directly to the hair and do not need an oxidative process to develop the color. Direct dyes are conventionally nitrophenylenediamines, nitroaminophenols, azo dyes, anthraquinones or indophenols. Direct dyes are known as anionic, cationic and nonionic direct dyes. The direct dyes are preferably used in an amount of 0.001 to 2 wt. %, relative to the entire application preparation.

Preferred anionic direct dyes are compounds known by the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Preferred cationic direct dyes are cationic triphenylmethane dyes, such as Basic Blue 7, Basic Blue 26, Basic Violet 2 and Basic Violet 14, aromatic systems which are substituted with a quaternary nitrogen group, such as Basic Yellow 57, Basic Red 76, Basic Blue 99, Basic Brown 16 and Basic Brown 17, cationic anthraquinone dyes, such as HC Blue 16 (Bluequat B) and direct dyes containing a heterocycle having at least one quaternary nitrogen atom, particularly Basic Yellow 87, Basic Orange 31 and Basic Red 51. Cationic direct dyes distributed under the trademark Arianor are preferred cationic direct dyes according to the invention.

Suitable nonionic direct dyes are in particular nonionic, nitro and quinone dyes and neutral azo dyes. Preferred nonionic direct dyes are the compounds known by the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2'-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenol)amino]-benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol.

Very particularly preferred lightening agents are those having at least one combination of tetrabromophenol blue and Acid Red 92.

Agents according to the invention can moreover contain further active ingredients, auxiliary substances and additives, such as nonionic polymers (e.g., vinylpyrrolidinone/vinyl acrylate copolymers, polyvinylpyrrolidinone, vinylpyrrolidinone/vinyl acetate copolymers, polyethylene glycols and polysiloxanes); additional silicones such as volatile or non-volatile, straight-chain, branched or cyclic, crosslinked or uncrosslinked polyalkylsiloxanes (e.g., dimethicones or cyclomethicones), polyarylsiloxanes and/or polyalkylarylsiloxanes, particularly polysiloxanes with organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; cationic polymers such as quaternized cellulose ethers, polysiloxanes with quaternary groups, dimethyldiallylammonium chloride polymers, acrylamide-dimethyldiallylammonium chloride copolymers, dimethylaminoethylmethacrylate methosulfate-vinylpyrrolidinone copolymers quaternized with diethyl sulfate, vinylpyrrolidinone-imidazolinium methochloride copolymers and quaternized polyvinyl alcohol; zwitterionic and amphoteric polymers; anionic polymers (e.g., polyacrylic acids or crosslinked polyacrylic acids); structuring agents such as glucose, maleic acid and lactic acid, hair-conditioning compounds, such as phospholipids, for example lecithin and cephalins; perfume oils, dimethyl isosorbide and cyclodextrins; active ingredients which improve fiber structure, particularly mono-, di- and oligosaccharides such as glucose, galactose, fructose, fruit sugar and lactose; dyes for coloring the agent; antidandruff active ingredients such as piroctone olamine, zinc omadine and climbazole; amino acids and oligopeptides, particularly arginine and/or serine; animal- or plant-based protein hydrolysates, such as elastin, collagen, keratin, silk and milk protein hydrolysates, or almond, rice, pea, potato and wheat protein hydrolysates, as well as in the form of the fatty acid condensation products or optionally anionically or cationically modified derivatives thereof; plant oils such as macadamia nut oil, palm oil, amaranth seed oil, peach stone oil, avocado oil, olive oil, coconut oil, rapeseed oil, sesame oil, jojoba oil, soy oil, peanut oil, evening primrose oil and tea tree oil; light stabilizers such as derivatized benzophenones, cinnamic acid derivatives and triazines; active ingredients such as panthenol, pantothenic acid, pantolactone, allantoin, pyrrolidinone carboxylic acids and the salts thereof and bisabolol; polyphenols, particularly hydroxycinnamic acids, 6,7-dihydroxycoumarins, hydroxybenzoic acids, catechins, tannins, leucoanthocyanidines, anthocyanidines, flavanones, flavones and flavonols; ceramides or pseudoceramides; vitamins, provitamins and vitamin precursors, particularly A, B3, B5, B6, C, E, F and H; plant extracts such as the extracts from aloe vera, angelica, aniseed, apricot, benzoin, bergamot, birch, stinging nettle, calamus, blackcurrant, costus, marsh mallow, oak bark, elemi, tarragon, pine-needle, galbanum, geranium, ginseng, grapefruit, guaiac wood, green tea, witch hazel, restharrow, hops, coltsfoot, ginger root, iris, jasmine, chamomile, cardamom, clover, burdock root, pine, kiwi fruit, coconut, coriander, caraway, mountain pine, lavender, lemongrass, lily, lime, lime blossom, litchi, mace, mallow, almond, mango, melissa, melon, meristem, myrrh, neroli, olibanum, opoponax, orange, patchouli, petitgrain, stone pine, wild thyme, rooibos, rose, rosemary, horse chestnut, sandalwood, sage, horsetail, yarrow, celery, fir, thyme, juniper, vine leaves, hawthorn, wheat, lady's smock, ylang-ylang, cedar and lemon; fats and waxes such as fatty alcohols, beeswax, montan wax and paraffins; swelling and penetrating substances such as glycerol, propylene glycol monoethyl ether, carbonates, hydrogencarbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3 distearate; pigments and propellants such as propane-butane mixtures, $N_2O$, dimethyl ether, $CO_2$ and air.

One skilled in the art selects these further substances according to the desired properties of the agents. Regarding further optional components and the quantities of these components used, reference is made to the relevant handbooks known to one skilled in the art. The additional active ingredients and auxiliaries are preferably used in agents according to the invention in amounts of 0.0001 to 10 wt. %, particularly 0.0005 to 5 wt. %, based on total weight of the application mixture.

The present invention further provides a method for lightening keratinic fibers, particularly human hair, wherein an agent of the first subject matter of the invention is applied onto the keratin-containing fibers, left on the fibers for 5 to 60 minutes, and then rinsed back out or washed out with a shampoo. The exposure time of the ready-to-use lightening agent is preferably 5 to 45 min, particularly 10 to 40 min, and more particularly 15 to 35 min. During the exposure time of the fiber to the agent it may be advantageous to assist the dyeing process by supplying heat. Heat can be supplied by an external heat source such as hot air from a hot air blower, and also, particularly when dyeing the hair of a living test subject, by the body temperature of the test subject. In the case of the latter possibility, the part dyed is conventionally covered with a cap. Exposure at room temperature is likewise according to the invention. In particular, the temperature during the exposure time is from 20° C. to 40° C., particularly from 25° C. to 38° C. The lightening agents provide good blonding and lightening results even at physiologically acceptable temperatures of below 45° C. After the end of the exposure time, the remaining lightening preparation is rinsed out from the hair with water or a cleaning agent. Conventional commercial shampoo can be used here as the cleaning agent, with it being possible to dispense with the cleaning agent and carry out the rinsing operation with water if the lightening agent has a carrier with a high surfactant content.

The present invention also provides for cosmetic use of an agent of the first subject matter of the invention for lightening keratin-containing fibers, particularly human hair.

The embodiments of the first subject matter of the invention apply mutatis mutandis to the method of the second subject matter of the invention and the use of the third subject matter of the invention.

No restrictions apply in principle to the packaging of the lightening agents according to the invention. The agents are conventionally packaged as single-component agents (A) which, optionally immediately before use, are mixed with a second preparation containing an oxidizing agent. It has, however, proved preferable for the product to be packaged as 2-component agent. The two preparations are mixed before use.

In order to prevent a premature, unwanted reaction of the phthalimides of general formula (I) with the oxidizing agent, the phthalimides of formula (I) are conveniently packaged separately from the oxidizing agent preparation and only brought into contact immediately before use.

The present invention therefore also provides an agent which is produced immediately before use by mixing at least two preparations, wherein the at least two preparations are provided in at least two separately packaged containers and in which one container contains an agent (A) containing in a cosmetic carrier at least one cationic phthalimide of general formula (I), and a further container containing an oxidizing agent preparation (B) comprising at least one oxidizing agent chosen from hydrogen peroxide and/or the addition compounds thereof onto organic or inorganic compounds. In order to offer the components of the ready-to-use lightening agent to the user in as convenient a presentation as possible, it is advisable to distribute the individual preparations together in one packaging unit.

The present invention accordingly also provides a multi-component packaging unit (kit of parts) for lightening keratinic fibers containing in separately packaged containers at least one oxidizing agent preparation (B) comprising hydrogen peroxide or a solid addition compound of hydrogen peroxide on inorganic or organic compounds, and at least one preparation (A) comprising at least one phthalimide of formula (I) in a cosmetic carrier.

In order to increase the lightening power, the multicomponent packaging unit may additionally contain at least one blonding preparation (C). A further embodiment of this subject matter of the invention is therefore a kit-of-parts which additionally contains in a separately packaged container at least one blonding powder (C) comprising at least one inorganic peroxodisulfate salt chosen from ammonium peroxodisulfate, potassium peroxodisulfate and/or sodium peroxodisulfate.

The components of the multiple packaging unit are packaged separately from one another in spatially different containers. The term "container" here is a receptacle, irrespective of the shape, material or closure thereof, which is capable of containing substances or substance mixtures. The term container therefore includes, without being limited thereto, the interior of a tube, a pouch or bag, a canister, a can, a tray, a bottle, a jar or a packet, a carton, a box, a wrapping or another container means. The containers can have a reclosable opening such as a screw closure. This can be of particular advantage should it be necessary to mix a plurality of agents intimately with one another before use by shaking.

The components of the lightening preparation can be present in a double chamber container with a separate or common opening. It is, however, preferred to divide them between different containers and to instruct the consumer to mix them with one another before use. The multicomponent packaging unit (kit of parts) additionally contains a set of instructions. The set of instructions in particular contains information, explanations and optionally illustrations for the consumer (male or female) for using the agents from the containers of the packaging unit in a method according to the second subject matter of the invention. It may furthermore be preferred for a mixing aid such as a dish, an application aid such as a comb or a brush, and/or personal protective equipment such as disposable gloves to also be enclosed in the kit.

The embodiments of the preceding subject matters of the invention also apply with respect to preferred embodiments of the multicomponent packaging unit according to the invention.

EXAMPLES

1. Synthesis Examples 1.1 Synthesis of 2-[2-(diethylamino)ethyl]-1H-isoindole-1,3(2H)-diol

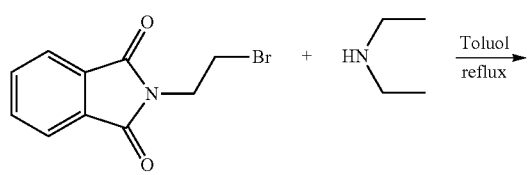

25.4 g (0.10 mol) of N-(2-bromoethyl)phthalimide were dissolved together with four times the molar quantity of diethylamine (29.2 g; 0.40 mol) in 500 ml of toluene and refluxed for 8 hours. After the reaction, excess diethylamine and the solvent were removed under a vacuum in a rotary evaporator. The residue was combined with tert-butyl methyl ether and the precipitated salt removed by filtration. The ether phase was then completely evaporated off. Yield: 21.0 g (85.4%).

1.2 Synthesis of 2-(1,3-dioxo-1,3-dihydro-2H-isoindol-2-yl)-N,N-diethyl-N-methylethanaminium p-toluenesulfonate (activator 5)

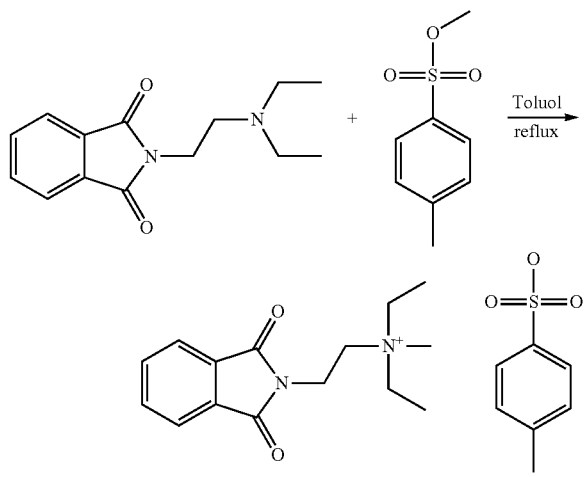

20.0 g (81.3 mmol) of 2-[2-(diethylamino)ethyl]-1H-isoindole-1,3(2H)-diol from stage 1 and 16.6 g (89.5 mmol) of p-toluenesulfonic acid methyl ester were refluxed in 250 ml toluene for 8 hours. After cooling, the white, crystalline solid was filtered out and rewashed with toluene. The product was then dried under a vacuum at 30° C. Yield: 10.3 g (29.3%); $^1$H-NMR (400 MHz, DMSO-$d_6$): δ [ppm]=1.39 (t, 6H); 2.28 (s, 3H); 3.06 (s, 3H); 3.47 (m, 6H); 3.97 (q, 2H); 7.10 (d, 2H); 7.48 (d, 2H); 7.89 (m, 4H); $^{13}$C-NMR (400 MHz, DMSO-$d_6$): δ [ppm]=8.1; 20.7; 30.5; 46.1; 55.5; 56.0; 123.2; 125.4; 128.0; 131.2; 134.5; 137.6; 145.6; 167.3.

2. Blondina Examples—Blonding Treatments with Hydrogen Peroxide 2.1 Production of a Blonding Cream Blonding creams were produced as follows from the listed components:

|  | wt. % | |
| --- | --- | --- |
| Raw material | Comp. 1 | Inv. 1 |
| Hydrenol D | 12.00 | 12.00 |
| Lorol techn. | 2.40 | 2.40 |
| Texapon NSO | 26.50 | 26.50 |
| Stabylen 30 | 0.10 | 0.10 |
| Cetiol OE | 2.40 | 2.40 |
| Turpinal SL | 0.20 | 0.20 |
| Sodium silicate 40/42 | 0.50 | 0.50 |
| Ammonium sulfate | 1.00 | 1.00 |
| Ammonia, 25% | 7.60 | 7.60 |
| 2-(1,3-Dioxo-1,3-dihydro-2H-isoindol-2-yl)-N,N-diethyl-N-methylethanaminium p-toluenesulfonate (activator 5) | — | 2.00 |
| Water | Ad 100 | Ad 100 |

Hydrenol® D INCI name: Cetearyl Alcohol (Cognis)
Lorol® techn. INCI name: Coconut Alcohol (Cognis)
Texapon® NSO approx. 27.5% active substance; INCI name: Sodium Laureth Sulfate (Cognis)
Stabylen® 30 INCI name: Acrylates/Vinylisodecanoate Crosspolymer (3V Sigma)
Cetiol OE INCI name: Dicaprylether (Cognis)
Turpinal® SL approx. 58-61% active substance content; INCI name: Etidronic Acid, Aqua (Solutia)

Hydrenol D and Lorol were melted together at 80° C., then Texapon NSO, Stabylen 30, Cetiol OE and Turpinal SL were stirred in in succession. Sodium silicate 40/42 and ammonium sulfate were in each case dissolved in a small quantity of water and likewise added with stirring. Finally, the ammonia was added at a temperature of approximately 40° C. The formulation was made up to 100 wt. % with water and stirred until cold.

2.2 Mixing with Developer Dispersion

The blonding creams produced in 2.1 were thoroughly mixed in a 1:1 ratio with a developer dispersion of the following composition.

| Raw material | wt. % |
| --- | --- |
| Ammonia, 25% | 0.62 |
| Dipicolinic acid | 0.10 |
| Disodium pyrophosphate | 0.03 |
| Turpinal SL | 1.50 |
| Texapon NSO | 2.00 |
| Dow Corning DB 110 A (nonionic silicone emulsion) | 0.07 |
| Aculyn 33A (acrylic polymer) | 12.00 |
| Hydrogen peroxide, 50% | 22.40 |
| Water | Ad 100 |

Aculyn® 33A approx. 28% solids content in water; INCI name: Acrylates Copolymer

Strands of dark blond, light brown and dark brown hair (codes: Kerling 7/0, Fischbach & Miller 6923 and Kerling 2/0) weighing approx. 0.7 g had 4 times the amount of the finished application mixture applied to them. Once the strands had been blonded for 30 min at 32° C., they were washed with a conventional commercial shampoo and dried with a hairdryer.

2.3 Evaluation of Lightening Power

Each strand of hair was measured colorimetrically before and after the bleaching operation. The ΔL value according to the following formula was used as a measure of lightening power:

$$\Delta L = L_{after} - L_{before}$$

$L_{after}$=lightness of the strands after bleaching
$L_{before}$=lightness of the strands before bleaching A duplicate determination was carried out for each formulation and each hair type, the mean in each case being calculated from the individual values. The greater the ΔL value, the better is the lightening power of the particular formulation.

2.4 Lightening Power with Activator 5

| Hair type | ΔL (formulation Comp. 1) | ΔL (formulation Inv. 1) | ΔΔL |
| --- | --- | --- | --- |
| Dark blond (Kerling 7/0) | 9.2 | 9.8 | 0.6 |
| Light brown (Fischbach & Miller 6923) | 8.7 | 9.4 | 0.7 |
| Dark brown (Kerling 2/0) | 3.5 | 4.6 | 1.1 |

Formulation Inv. 1 according to the invention achieves distinctly improved lightening power on all hair types.

We claim:
1. An agent for lightening keratinic fibers comprising, in a cosmetic carrier:
(i) at least one oxidizing agent chosen from hydrogen peroxide and/or one of the solid addition products thereof onto organic or inorganic compounds, and
(ii) at least one cationic phthalimide according to formula (I),

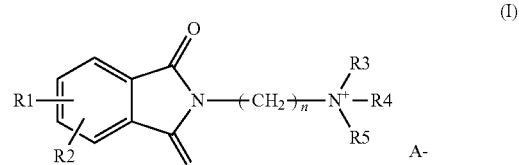

wherein
R1 and R2 are each mutually independently a hydrogen atom, a halogen atom, a $C_1$-$C_6$ alkyl group, a partially or completely halogenated $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group, a nitrile group, a nitroso group, a nitro group, a carboxylic acid group, a sulfonic acid group, a sulfonamido group, an amino group, a di-$C_1$-$C_6$-alkylamino group, a mono-$C_1$-$C_6$-alkylamino group, a $C_1$-$C_6$ alkoxycarbonyl group, an optionally substituted aryl group, or an optionally substituted heteroaryl group, or
R1 and R2 form, together with the adjacent benzene ring, a further phthalimide unit according to formula (Ia),

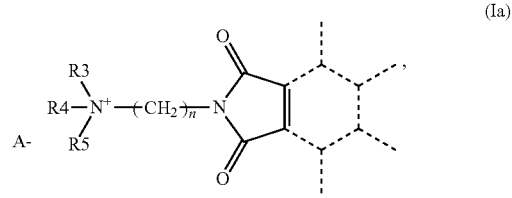

R3, R4, R5 are each mutually independently a $C_1$-$C_6$ alkyl group, a partially or completely halogenated $C_1$-$C_6$ alkyl group, a $C_2$-$C_6$ alkenyl group, a $C_2$-$C_6$ hydroxyalkyl group, a $C_2$-$C_6$ polyhydroxyalkyl group, a $C_1$-$C_6$-alkoxy-$C_2$-$C_6$-alkyl group, a cyano-$C_1$-$C_6$-alkyl group, an aryl-$C_1$-$C_6$-alkyl group, a carboxy-$C_1$-$C_6$-alkyl group or a sulfonyl-$C_1$-$C_6$-alkyl group, or two of the substituents R3, R4 and R5 form, together with the attached nitrogen, a 5-, 6- or 7-membered, saturated or unsaturated ring which optionally contains further heteroatoms, n is an integer from 1 to 6, and A⁻ is a physiologically acceptable anion.

2. The agent according to claim 1, wherein the phthalimide according to formula (I) is at least a compound wherein R1 and R2 are each mutually independently a hydrogen atom, a halogen atom, a hydroxyl group, a $C_1$-$C_6$ alkoxy group, or R1 and R2 form, together with the adjacent benzene ring, a further phthalimide unit according to formula (Ia).

3. The agent according to claim 1, wherein the phthalimide according to formula (I) is at least a compound wherein R3, R4 and R5 are each mutually independently a $C_1$-$C_6$ alkyl group, a $C_2$-$C_6$ alkenyl group, or a $C_2$-$C_6$ hydroxyalkyl group.

4. The agent according to claim 1, wherein the phthalimide according to formula (I) is at least a compound chosen from physiologically acceptable salts, the cationic moieties of which are formed of salts of 2-(1,3-dioxo-1,3-dihydro-2-isoindol-2-yl)-N,N,N-trimethylethanaminium, salts of 2-(1,3-dioxo-1,3-dihydro-2H-isoindol-2-yl)-N,N-diethyl-N-methylethanaminium, salts of N-[2-(1,3-dioxo-1,3-dihydro-2H-isoindol-2-yl)ethyl]-N,N-diethylprop-2-en-1-aminium, salts of N-allyl-N-[2-(1,3-dioxo-1,3-dihydro-2H-isoindol-2-yl)ethyl]-N-methylprop-2-en-1-aminium, salts of N-[2-(1,3-dioxo-1,3-dihydro-2H-isoindol-2-yl)ethyl]-N-methyl-N-propylpropan-1-aminium, salts of N-[2-(1,3-dioxo-1,3-dihydro-2H-isoindol-2-yl)ethyl]-N,N-dipropylprop-2-en-1-aminium, salts of 3-(1,3-dioxo-1,3-dihydro-2H-isoindol-2-yl)-N,N,N-trimethylpropan-1-aminium, salts of N-[3-(1,3-dioxo-1,3-dihydro-2H-isoindol-2-yl)propyl]-N,N-dimethylprop-2-en-1-aminium, salts of 3-(1,3-dioxo-1,3-dihydro-2H-isoindol-2-yl)-N,N-diethyl-N-methylpropan-1-aminium and salts of N-[3-(1,3-dioxo-1,3-dihydro-2H-isoindol-2-yl)propyl]-N,N-diethylprop-2-en-1-aminium.

5. The agent according to claim 1, wherein the phthalimide according to formula (I) is at least a compound chosen from 2-(1,3-dioxo-1,3-dihydro-2H-isoindol-2-yl)-N,N-diethyl-N-methylethanaminium p-toluenesulfonate, N-allyl-N-[2-(1,3-dioxo-1,3-dihydro-2H-isoindol-2-yl)ethyl]-N-methylprop-2-en-1-aminium p-toluenesulfonate and N-[2-(1,3-dioxo-1,3-dihydro-2H-isoindol-2-yl)ethyl]-N-methyl-N-propylpropan-1-aminium p-toluenesulfonate.

6. The agent according to claim 1, wherein the phthalimide(s) according to formula (I) is/are present in an amount of 0.01 to 25 wt. %, based on total weight of the ready-to-use agent.

7. The agent according to claim 6, wherein the phthalimide(s) according to formula (I) is/are present in an amount of 0.1 to 10 wt. %, based on total weight of the ready-to-use agent.

8. The agent according to claim 1, wherein the oxidizing agent is at least hydrogen peroxide in the form of an aqueous solution.

9. The agent according to claim 1 further comprising at least one inorganic persulfate or peroxodisulfate salt.

10. The agent according to claim 9, wherein the at least one inorganic persulfate or peroxodisulfate salt is chosen from ammonium peroxodisulfate, potassium peroxodisulfate and/or sodium peroxodisulfate.

11. A method of lightening keratin-containing fibers comprising applying an agent according to claim 1 onto the keratin-containing fibers.

12. A multicomponent packaging unit for lightening keratinic fibers comprising, in separately packaged containers:

at least one oxidizing agent preparation (B) containing hydrogen peroxide or a solid addition compound of hydrogen peroxide on inorganic or organic compounds, and at least one preparation (A) containing at least one phthalimide according to formula (I)

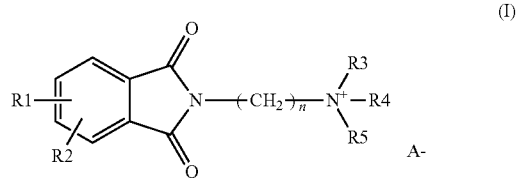

in a cosmetic carrier.

* * * * *